United States Patent [19]

Chan

[11] Patent Number: 5,139,034

[45] Date of Patent: Aug. 18, 1992

[54] SMOKING COMPOSITIONS CONTAINING A MENTHOL-RELEASE ADDITIVE

[75] Inventor: W. Geoffrey Chan, Chesterfield, Va.

[73] Assignees: Philip Morris Incorporated, New York, N.Y.; Philip Morris Products Inc., Richmond, Va.

[21] Appl. No.: 613,013

[22] Filed: Nov. 15, 1990

[51] Int. Cl.$^5$ .......................... A24B 3/12; C07H 13/02
[52] U.S. Cl. ..................... 131/277; 131/278; 536/6; 536/119; 127/30
[58] Field of Search .............. 131/277; 536/6, 119; 127/30

Primary Examiner—V. Millin
Attorney, Agent, or Firm—James E. Schardt; George A. Depaoli

[57] ABSTRACT

In one embodiment, this invention provides a smoking composition which contains a flavorant additive which releases menthol under normal cigarette smoking conditions.

The menthol-release additive is a mixture of menthyloxycarbonylglucose compounds which include more than 35 mole percent of 1-O-menthyloxycarbonyl-$\beta$-D-glucopyranose and more than about 20 mole percent of 1,6-di-O-menthyloxycarbonyl-$\beta$-D-glucopyranose.

19 Claims, No Drawings

5,139,034

SMOKING COMPOSITIONS CONTAINING A MENTHOL-RELEASE ADDITIVE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; 3,379,754; and the like.

J. C. Leffingwell et al "Tobacco Flavoring For Smoking Products" (R.J. Reynolds publication, 1972) recites a listing of desirable flavorants for smoking compositions, which include phenols, terpenols and lactones such as guaiacol, 1-undecanol and 5-dodecalactone.

The high degree of volatility and ease of sublimation of flavorant additives in tobacco products have presented problems in the manufacturing operations, and have resulted in a decreased shelf-life of the products due to losses of flavorant by evaporation on storage.

Recent developments have involved incorporating a low volatility organic additive in a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as l-menthyl linalool carbonate. Under smoking conditions pyrolysis of the carbonate ester releases menthol which flavors the mainstream smoke.

U.S. Pat. Nos. 4,119,106; 4,171,702; 4,177,339; and 4,212,310 describe oligomeric and polymeric carbonates ester derivatives which as constituents of smoking compositions are stable and non-volatile under storage conditions, and are adapted to release pyrolysis products under smoking conditions that improve the taste and aroma of the smoke.

Of particular interest with respect to the present invention are U.S. Pat. Nos. 3,332,428 and 3,419,543 that describe smoking tobacco compositions which contain a menthyl carbonate ester of a glycol and saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

There is continuing research effort to develop low delivery smoking compositions which generate mainstream smoke with enhanced taste and character under smoking conditions.

Accordingly, it is an object of this invention to provide smoking compositions having incorporated therein a flavorant-release component which is characterized by lack of mobility and/or volatility at ambient temperature.

It is another object of this invention to provide smoking tobacco compositions having incorporated therein a menthol-release additive which under normal smoking conditions imparts improved flavor to mainstream smoke and improved aroma to sidestream smoke.

It is a further object of this invention to provide a novel menthyloxycarbonlglucose mixture, and an improved process for producing the mixture.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001–5 weight percent, based on the total weight of filler, of a menthol-release additive which is a mixture of menthyloxycarbonylglucose compounds comprising (a) more than about 35 mole percent of 1-O-menthyloxycarbonyl-$\beta$-D-glucopyranose; (b) more than about 20 mole percent of 1,6-di-O-menthyloxycarbonyl-$\beta$-D-glucopyranose; (c) less than about 20 mole percent of 6-O-menthyloxycarbonyl-D-glucose; (d) less than about 15 mole percent of 2-O-menthyloxycarbonyl-D-glucose; and (e) less than about 10 mole percent of 2,6-di-O-menthyloxycarbonyl-D-glucose.

In a preferred embodiment, the smoking composition additives is a mixture of menthyloxycarbonylglucose compounds as described above which contains between about 35–65 mole percent of a 1-O-menthyloxycarbonyl-$\beta$-D-glucopyranose and between about 20–65 mole percent of 1,6-di-O-menthyloxycarbonyl-$\beta$-D-glucopyranose.

The invention menthol-release additive mixture of menthyloxycarbonylglucose compounds can be obtained directly by an improved process embodiment as elaborated hereinbelow. Alternatively, the mixture can be formulated from the individual constituent menthylcarbonylglucose compounds which previously had been synthesized and recovered as separate isomers.

In another embodiment, this invention provides a smoking composition comprising an admixture of (1) combustible filler selected from natural tobacco, reconstituted tobacco and tobacco substitutes, and (2) between about 0.0001–5 weight percent, based on the total weight of filler, of a menthol-release additive corresponding to the formula:

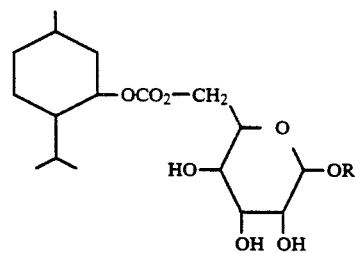

where R is a $C_1$–$C_{10}$ hydrocarbyl substituent.

Illustrative of the R substituent are methyl, ethyl, butyl, hexyl, cyclohexyl, octyl, phenyl, benzyl, phenethyl, and the like.

In another embodiment, this invention provides a mixture of menthyloxycarbonylglucose compounds comprising (a) more than about 35 mole percent of 1-O-menthyloxycarbonyl-$\beta$-D-glucopyranose; (b) more than about 20 mole percent of 1,6-di-O-menthyloxycarbonyl-$\beta$-D-glucopyranose; (c) less than about 20 mole percent of 6-O-menthyloxycarbonyl-D-glucose; (d) less than about 15 mole percent of 2-O-menthyloxycarbonyl-D-glucose; and (e) less than about 10 mole percent of 2,6-di-O-menthyloxycarbonyl-D-glucose; wherein the mixture in powder form is a free-flowing bulk material.

A present invention menthyloxycarbonylglucose compound which is incorporated as previously described is a low volatility organic material which under normal smoking conditions pyrolyzes and releases free menthol as a volatile constituent which enhances the flavor and aroma of low delivery cigarette smoke.

SYNTHESIS OF MENTHYLOXYCARBONYLGLUCOSES

In another embodiment this invention provides a process for producing a mixture of menthyloxycarbonylglucose compounds containing at least about 35 mole percent of 1-O-menthyloxycarbonyl-β-D-glucopyranose which comprises reacting glucose with menthyl chloroformate in an organic solvent medium in contact with a catalyst having the formula:

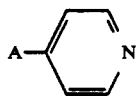

where A is a tertiary amine substituent containing between about 2-6 carbon atoms.

The esterification reaction is conducted at a temperature between about $-20°$ and $60°$ C. for a period of about 0.5-24 hours as necessary to complete the reaction. The reaction medium consists of one or more solvents such as dioxane, tetrahydrofuran, dimethylformamide, carbon disulfide, dimethylsulfoxide, acetone, acetonitrile, pyridine, and the like.

An important aspect of the esterification reaction is the presence of a 4-tertiary-amine-substituted pyridine catalyst. Illustrative of tertiaryamine-substituted pyridine catalysts are 4-dimethylaminopyridine, 4-(1-pyrrolidino)pyridine, 4-(1-piperidino)pyridine, 4-(1-hexahydroazepino)pyridine, 4-(4-morpholino)pyridine, 4-(4-methyl-1-piperidinyl)pyridine, and the like.

The catalyst is utilized in a quantity between about 0.25-1.5 moles per mole of menthyl chloroformate employed in the esterification reaction.

The use of a 4-tertiary-amine-substituted pyridine as an acylation catalyst is described in literature such as Chem. Soc. Rev. 12, 129 (1983), and U.S. Pat. Nos. 3,678,082 and 4,540,743.

Preparation of Tobacco Compositions

In a further embodiment the present invention provides a method for preparing a smoking composition which is adapted to impart flavor and aroma to mainstream and sidestream smoke under smoking conditions, which method comprises incorporating into natural tobacco, reconstituted tobacco or tobacco substitute between about 0.0001-5 weight percent, based on composition weight, of a menthol-release additive which is (1) a mixture of menthyloxycarbonylglucose compounds comprising (a) more than about 35 mole percent of 1-O-menthyloxycarbonyl-β-D-glucopyranose; (b) more than about 20 mole percent of 1,6-di-O-menthyloxycarbonyl-β-D-glucopyranose; (c) less than about 20 mole percent of 6-O-menthyloxycarbonyl-D-glucose; (d) less than about 15 mole percent of 2-O-menthyloxycarbonyl-D-glucose; and (e) less than about 10 mole percent of 2,6-di-O-menthyloxycarbonyl-D-glucose; or (2) a menthyloxycarbonylglucose compound corresponding to the formula:

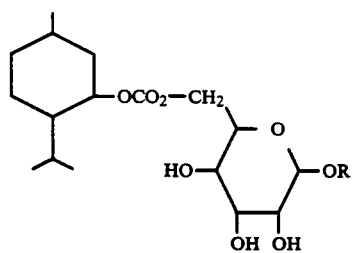

where R is a $C_1$-$C_{10}$ hydrocarbyl substituent.

The invention menthol-release additive can be incorporated into the tobacco or tobacco substitute in accordance with methods known and used in the art. Preferably the menthol-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant additive may be incorporated as part of a concentrated tobacco extract which is applied to a fibrous tobacco web as in the manufacture of reconstituted tobacco. Another suitable procedure is to incorporate the flavorant additive in tobacco or tobacco substitute filler in a concentration between about 0.5-5 weight percent, based on the weight of filler, and then subsequently to blend the treated filler with filler which does not contain flavorant additive.

The term "tobacco substitute" is meant to include nontobacco smoking filler materials such as are disclosed in U.S. Pat. Nos. 3,703,177; 3,796,222, 4,019,521; 4,079,742; and references cited therein; incorporated herein by reference.

The following Examples are further illustrative of the present invention. The specific ingredients and processing parameters are presented as being typical, and various modifications can be derived in view of the foregoing disclosure within the scope of the invention.

EXAMPLE I

D-Glucose (186 g, 1.03 mole) was added to 2.5 L of pyridine, and the mixture was heated to 65° C. The resulting solution was cooled to 5° C., and l-menthyl chloroformate (236 g, 1.08 mole) was added dropwise over 3 hours. The resulting mixture was stirred for about 18 hours, then the solvent was removed by rotary evaporation under vacuum. The residual viscous syrup was shaken with ethyl acetate (500 ml)/water (500 ml). The resultant organic phase was diluted with n-hexane (500 ml) and washed successively with 10% hydrochloric acid (pH=1), water, dilute NaHCO₃, and water. The organic phase then was concentrated by rotary evaporation to a viscous syrup, and the syrup was dissolved in 95% ethanol. n-Hexane (500 ml) and water (250 ml) were added, and the mixture was shaken thoroughly. The aqueous layer was extracted further with n-hexane, and then treated with decolorizing charcoal. The charcoal was filtered off, and the filtrate was concentrated to a viscous syrup by rotary evaporation. The residue was dried under 100 millitorr vacuum. The residual product was a glassy immobile syrup, 290 g (77% yield).

| | |
|---|---|
| 2,6-di-O-menthyloxycarbonyl-D-glucose | 15% |
| 1,6-di-O-menthyloxycarbonyl-β-D-glucopyranose | 13% |
| 2-O-menthyloxycarbonyl-D-glucose | 11% |
| 1-O-menthyloxycarbonyl-β-D-glucopyranose | 14% |
| 6-O-menthyloxycarbonyl-D-glucose | 47% |

EXAMPLE II

Glucose (3.6 g, 20 mmole) was dissolved in pyridine (50 ml) and cooled in an ice-acetone bath. Menthyl chloroformate (2.2 g, 10 mmole) in 10 ml dichloromethane was added dropwise over 30 minutes. The mixture was warmed to room temperature slowly and then stirred at room temperature for about 18 hours. The solvent was removed by rotary evaporation, and the residual syrup was dissolved in 30 ml of ethyl acetate and 10 ml of water. Hexane (20 ml) was added and the mixture was shaken thoroughly. The organic layer was then washed with water, and the solvent was removed by rotary evaporation. The resultant syrup was dissolved in 10 ml of 95% ethanol and 5 ml of water. The solution was extracted with hexane, and the solvent was removed by rotary evaporation. After drying under 100 millitorr vacuum, the rigid foam product collapsed to a glassy immobile syrup upon exposure to air (2.65 g).

| | |
|---|---|
| 2,6-di-O-menthyloxycarbonyl-D-glucose | 4% |
| 1,6-di-O-menthyloxycarbonyl-β-D-glucopyranose | 3% |
| 2-O-menthyloxycarbonyl-D-glucose | 18% |
| 1-O-menthyloxycarbonyl-β-D-glucopyranose | 17% |
| 6-O-menthyloxycarbonyl-D-glucose | 59% |

EXAMPLE III

Glucose (3.6 g, 20 mmole) was dissolved in dimethylformamide (40 ml) and pyridine (5 ml), and cooled in an ice-acetone bath. Menthyl chloroformate (2.2 g, 10 mmole) in 10 ml dichloromethane was added dropwise over 30 minutes. The mixture was warmed to room temperature slowly and then stirred at room temperature for about 18 hours. Water (2 ml) was added and the mixture was stirred for 30 minutes. The solvent was removed by Kugelrohl distillation at 250 millitorr vacuum (50° C.) to a viscous syrup, and the syrup was dissolved in 30 ml of ethyl acetate and 10 ml of water. Hexane (20 ml) was added and the mixture was shaken thoroughly. The organic layer was washed with water and then with saturated sodium chloride solution. The solvent was removed by rotary evaporation. After drying under 100 millitorr vacuum, the rigid foam product collapsed to a glassy immobile syrup upon exposure to air (2.8 g).

| | |
|---|---|
| 2,6-di-O-menthyloxycarbonyl-D-glucose | 11% |
| 1,6-di-O-menthyloxycarbonyl-β-D-glucopyranose | 3% |
| 2-O-menthyloxycarbonyl-D-glucose | 25% |
| 1-O-menthyloxycarbonyl-β-D-glucopyranose | 13% |
| 6-O-menthyloxycarbonyl-D-glucose | 47% |

EXAMPLE IV

Glucose (3.6 g, 20 mmole) was dissolved in dimethylformamide (20 ml), and dioxane (20 ml) and pyridine (5 ml) were added. The solution was cooled in an ice-acetone bath, and menthyl chloroformate (2.2 g, 10 mmole) in 10 ml of dichloromethane was added dropwise over 30 minutes. The mixture was warmed to room temperature slowly and then stirred at room temperature for about 18 hours. Water (2 ml) was added and the mixture was stirred for 30 minutes. The solvent was removed by Kugelrohl distillation at 250 millitorr vacuum (50° C.) to a viscous syrup, and the syrup was dissolved in 30 ml of ethyl acetate and 10 ml of water. Hexane (20 ml) was added and the mixture was shaken thoroughly. The organic layer was washed with water and then with saturated sodium chloride solution. The solvent was removed by rotary evaporation, and after drying under 100 millitorr vacuum the rigid foam product collapsed to a glassy immobile syrup upon exposure to air (2.9 g).

| | |
|---|---|
| 2,6-di-O-menthyloxycarbonyl-D-glucose | 8% |
| 1,6-di-O-menthyloxycarbonyl-β-D-glucopyranose | 5% |
| 2-O-menthyloxycarbonyl-D-glucose | 18% |
| 1-O-menthyloxycarbonyl-β-D-glucopyranose | 17% |
| 6-O-menthyloxycarbonyl-D-glucose | 52% |

EXAMPLE V

Glucose (3.6 g, 20 mmole) was dissolved in pyridine (50 ml). Dimethylaminopyridine (305 mg, 2.5 mmole) was added and the solution was cooled in an ice-acetone bath. Menthyl chloroformate (2.2 g, 10 mmole) in 10 ml dichloromethane was added dropwise over 30 minutes, and the mixture was warmed to room temperature slowly and then stirred at room temperature for about 18 hours. Water (2 ml) was added and the mixture was stirred for 30 minutes. The solvent was removed by rotary evaporation to a viscous syrup, and the syrup was dissolved in 30 ml of ethyl acetate and 10 ml of water. Hexane (20 ml) was added and the mixture was shaken thoroughly. The organic layer was washed successively with water, 10% hydrochloric acid, water, and saturated sodium chloride solution. The solvent was removed by rotary evaporation, and after drying under 100 millitorr vacuum the rigid foam product collapsed to a glassy immobile syrup upon exposure to air (2.9 g).

| | |
|---|---|
| 2,6-di-O-menthyloxycarbonyl-D-glucose | 7% |
| 1,6-di-O-menthyloxycarbonyl-β-D-glucopyranose | 5% |
| 2-O-menthyloxycarbonyl-D-glucose | 17% |
| 1-O-menthyloxycarbonyl-β-D-glucopyranose | 17% |
| 6-O-menthyloxycarbonyl-D-glucose | 55% |

EXAMPLE VI

Glucose (3.6 g, 20 mmole) was dissolved in pyridine (50 ml). Dimethylaminopyridine (1.22 g, 10 mmole) was added, and the solution was cooled in an ice-acetone bath. Menthyl chloroformate (2.2 g, 10 mmole) in 10 ml of dichloromethane was added dropwise over 30 minutes. The mixture was warmed to room temperature slowly and then stirred at room temperature for about 18 hours. Water (2 ml) was added and the mixture was stirred for 30 minutes. The solvent was removed by rotary evaporation to a viscous syrup, and the syrup was dissolved in 30 ml of ethyl acetate and 10 ml of water. Hexane (20 ml) was added and the mixture was shaken thoroughly. The organic layer was then washed successively with 10% hydrochloric acid, water, and saturated sodium chloride solution. The solvent was removed by rotary evaporation, and after drying under 100 millitorr vacuum a rigid foam product (2.8 g) was obtained which was hygroscopic when exposed to moisture.

| | |
|---|---|
| 2,6-di-O-menthyloxycarbonyl-D-glucose | 8% |
| 1,6-di-O-menthyloxycarbonyl-β-D-glucopyranose | 11% |
| 2-O-menthyloxycarbonyl-D-glucose | 11% |
| 1-O-menthyloxycarbonyl-β-D-glucopyranose | 35% |
| 6-O-menthyloxycarbonyl-D-glucose | 35% |

EXAMPLE VII

Glucose (3.6 g, 20 mmole) was dissolved in dimethylformamide (40 ml). Dimethylaminopyridine (1.22 g, 10 mmole) was added, and the solution was cooled in an ice-acetone bath. Menthyl chloroformate (2.2 g, 10 mmole) in 10 ml of dichloromethane was added dropwise over 30 minutes. The mixture was warmed to room temperature slowly and then stirred at room temperature for about 18 hours. Water (2 ml) was added and the mixture was stirred for 30 minutes. The solvent was removed by rotary evaporation to a viscous syrup, and the syrup was dissolved in 30 ml of ethyl acetate and 10 ml of water. Hexane (20 ml) was added and the mixture was shaken thoroughly. The organic layer was washed successively with water, 10% hydrochloric acid, water, and saturated sodium chloride solution. The solvent was removed by rotary evaporation, and after drying under 100 millitorr vacuum a rigid foam product (2.8g) was obtained which was hygroscopic when exposed to moisture.

| | |
|---|---|
| 2,6-di-O-menthyloxycarbonyl-D-glucose | 9% |
| 1,6-di-O-menthyloxycarbonyl-β-D-glucopyranose | 10% |
| 2-O-menthyloxycarbonyl-D-glucose | 14% |
| 1-O-menthyloxycarbonyl-β-D-glucopyranose | 38% |
| 6-O-menthyloxycarbonyl-D-glucose | 29% |

EXAMPLE VIII

The Example illustrates the preparation of an invention menthol glucose carbonate mixture in the form of a free-flowing powder in accordance with the present invention.

Glucose (3.6 g, 20 mmole) was dissolved in dimethylformamide (40 ml). Dimethylaminopyridine (2.44 g, 20 mmole) was added, and the solution was cooled in an ice-acetone bath. Menthyl chloroformate (4.4 g, 20 mmole) in 10 ml of dichloromethane was added dropwise over 30 minutes. The mixture was warmed to room temperature slowly and then stirred at room temperature for about 18 hours. Water (2 ml) was added and the mixture was stirred for 30 minutes. The solvent was removed by rotary evaporation to a viscous syrup, and the syrup was dissolved in 30 ml of ethyl acetate and 10 ml of water. Hexane (20 ml) was added and the mixture was shaken thoroughly. The organic layer was washed successively with water, 10% hydrochloric acid, water, and saturated sodium chloride solution. The solvent was removed by rotary evaporation and after drying under 100 millitorr vacuum, a rigid foam product (3.2 g) was obtained which formed a free-flowing powder when ground.

| | |
|---|---|
| 2,6-di-O-menthyloxycarbonyl-D-glucose | 9% |
| 1,6-di-O-menthyloxycarbonyl-β-D-glucopyranose | 24% |
| 2-O-menthyloxycarbonyl-D-glucose | 13% |
| 1-O-menthyloxycarbonyl-β-D-glucopyranose | 38% |
| 6-O-menthyloxycarbonyl-D-glucose | 17% |

EXAMPLE IX

High performance liquid chromatographic analysis of each menthol glucose carbonate reaction mixture described in Examples I-VIII was performed with a Waters Associates 600A Solvent Delivery System, Rheodyne 7125 injector, Waters Associates R401 Differential Refractometer, and a Hewlett Packard 3390A recording integrator. The column was a 4.6 mm×250 mm stainless steel column packed with 10μ Zorbax $NH_2$ material. The eluting solvent was 10% methanol in acetonitrile with 0.5% water added.

A 100 mg sample of the products obtained from Examples I-VIII and 10 mg of benzyl 6-O-menthyloxycarbonyl-β-D-glucopyranoside (internal standard) each were dissolved in 2 ml of acetonitrile/methanol/water (89/10/1).

The response factor of each of the 5 saccharide isomers were first determined by dissolving 10 mg of the isomer and 10 mg of the internal standard in the same solvent solution, and comparing the peak area of each isomer with respect to the internal standard. The sample solutions were injected into the HPLC column, and five peaks corresponding to the 5 isomers in each mixture plus the peak for the internal standard were observed. The composition of each Example mixture was calculated based on the relative intensity of each peak in relation to the internal standard.

EXAMPLE X

Isolation of the 5 menthyloxycarbonylglucose isomers by preparative HPLC was performed with a Waters Associates 590EF Solvent Delivery System, Waters Associates U6K injector, Waters Associates R401 Differential Refractometer, ISCO 2150 Peak Separator, ISCO Foxy fraction collector, and a Linear 1100 recorder. The column was a 22 mm×250 mm stainless steel column packed with 10μRSil $NH_2$ material. The eluting solvent was 7.5% water in acetonitrile.

A saturated solution of product (Example I) in the eluting solvent was injected into the column, and the 5 peaks corresponding to the 5 isomers were collected in the order of elution. Each fraction was concentrated to either a solid or a syrup and then recrystallized with 95% ethanol to provide an analytically pure solid.

Each of the pure solids was characterized by spectroscopic methods and elemental analysis, and the results were consistent with each assigned structure.

The following are the $^{13}$C-NMR chemical shift data for the anomeric carbons for each of the 5 isomers:

| | Assignment |
|---|---|
| 2,6-MCG | |
| 96.26 | β-C-1 |
| 91.15 | α-C-1 |
| 1,6-β-MCG | |
| 98.92 | C-1 |
| 2-MCG | |
| 96.25 | β-C-1 |
| 91.11 | α-C-1 |
| 1-β-MCG | |
| 99.15 | C-1 |

|  | Assignment |
| --- | --- |
| 6-MCG | |
| 98.18 | β-C-1 |
| 93.95 | α-C-1 |

The following are the $^{13}$C-NMR chemical shift data for the carbonate carbons for each of the 5 isomers:

|  | Assignment |
| --- | --- |
| 2,6-MCG | |
| 156.46 | α-C-6-Carbonyl |
| 156.39 | β-C-6 Carbonyl |
| 156.27 | β-C-2 Carbonyl |
| 156.13 | α-C-2 Carbonyl |
| 1,6-β-MCG | |
| 156.28 | C-6 Carbonyl |
| 155.15 | C-1 Carbonyl |
| 2-MCG | |
| 156.30 | (β)-Carbonyl |
| 156.16 | (α)-Carbonyl |
| 1-β-MCG | |
| 155.32 | Carbonyl |
| 6-MCG | |
| 156.50 | (α)-Carbonyl |
| 156.42 | (β)-Carbonyl |

EXAMPLE XI

The Example illustrates the relative menthol-delivery efficiency of menthyloxycarbonyl-D-glucose compounds when pyrolyzed at 300° C.

The compounds together with phenethyl 6-O-menthyloxycarbonyl-β-D-glucoside were pyrolyzed in the injector port of a Hewlett Packard 5880A gas chromatograph, and the amount of free menthol was analyzed by GC on a 60 m×0.32 mm ID DB-5 column.

Each compound was dissolved in 2 ml of methylene chloride with dodecane as an internal standard. The injector temperature was set at 300° C., and the sample was introduced into the injector, and held in the injector zone for 2 minutes before the splitter was opened to release the volatile mixture.

The pyrolysis results were as follows:

|  | MENTHOL | |
| --- | --- | --- |
|  | mg/mg[1] | %[2] |
| 6-O-Menthyloxycarbonyl-D-glucose | 0.18 | 41.3 |
| 1-O-Menthyloxycarbonyl-β-D-glucose | 0.26 | 59.5 |
| 2-O-Menthyloxycarbonyl-D-glucose | 0.14 | 32.1 |
| 1,6-Di-O-menthyloxycarbonyl-β-D-glucose | 0.22 | 38.6 |
| 2,6-Di-O-menthyloxycarbonyl-D-glucose | 0.16 | 27.8 |
| Phenethyl 6-O-menthyloxycarbonyl-β-D-glucoside | 0.05 | 14.7 |

[1]mg of menthol per mg of sample.
[2]percent of total available menthol.

EXAMPLE XII

This Example illustrates the relative menthol-delivery efficiency of menthyloxycarbonylglucose compounds as tobacco filler additives under cigarette smoking conditions.

The 5 isomeric menthyloxycarbonylglucose compounds and phenethyl 6-O-menthyloxycarbonyl-β-D-glucoside were each fabricated into cigarettes at a 2% load level, based on the weight of cigarette filler. Each cigarette contained approximately 18 mg of additive, of which 13 mg was consumed during smoking (the weight of filler was about 900 mg and the 83 mm cigarette was smoked to a nominal 23 mm butt length). The total available menthol after smoking was 7.4 mg for the dicarbonates, 5.6 mg for the monocarbonates and 4.4 mg for phenethyl 6-O-menthyloxycarbonyl-β-D-glucoside. The cigarettes were smoked on a smoking machine and the amount of menthol on the TPM pad was analyzed by standard procedure.

| Menthol in Main Stream Smoke (mg/cig) (Menthyloxycarbonylglucose Isomers on Cigarette Filler) | | | |
| --- | --- | --- | --- |
|  | Tar | Menthol | %[1] |
| 6-O-Menthyloxycarbonyl-D-glucose | 9 | 0.48 | 8.6 |
| 1-O-Menthyloxycarbonyl-β-D-glucose | 8 | 0.61 | 10.9 |
| 2-O-Menthyloxycarbonyl-D-glucose | 7 | 0.41 | 7.3 |
| 1,6-Di-O-menthyloxycarbonyl-β-D-glucose | 9 | 0.67 | 9.1 |
| 2,6-Di-O-menthyloxycarbonyl-D-glucose | 10 | 0.31 | 4.2 |
| Phenethyl 6-O-menthyloxycarbonyl-β-D-glucoside | 11 | 0.50 | 11.5 |

[1]percent of total available menthol.

EXAMPLE XIII

Phenethyl 1-O-Menthyloxycarbonyl-β-D-glucoside

A 100 ml round-bottomed flask was charged with phenethyl β-D-glucoside (1.14 g, 4 mmole) and 15 ml of dioxane, and the flask was cooled in an ice-water bath. Pyridine (0.633 g, 8 mmole) in 5 ml of dichloromethane was added, and menthyl chloroformate (0.892 g, 4 mmole) in 20 ml of dioxane was added dropwise to the glucoside solution over a 45 minute period. The temperature was increased slowly to room temperature and the mixture was stirred at room temperature for about 18 hours. The solvent was removed by rotary evaporation under vacuum, and then water (20) and dichloromethane (50 ml) were added and the mixture was stirred for 30 minutes. The organic phase was washed with water and saturated sodium chloride solution, and dried over magnesium sulfate. After removal of the solvent, the solid residue was recrystallized from 95% ethanol to provide the title product, 1.23 g (66% yield). NMR and IR spectra confirmed the structure.

EXAMPLE XIV

Benzyl 6-O-Menthyloxycarbonyl-β-D-glucoside

A 500 ml round-bottom flask was charged with benzyl β-D-glucoside (6.8 g, 25 mmole) and 75 ml of dioxane, and the flask was cooled in an ice-water bath. Pyridine (3.9 g, 50 mmole) in 10 ml of dichloromethane was added, and menthyl chloroformate (5.46 g, 25 mmole) in 100 ml of dioxane was added dropwise to the glucoside solution over a 45 minute period. The temperature was increased slowly to room temperature and the mixture was stirred at room temperature for about 18 hours. The solvent was removed by rotary evaporation under vacuum, and water (100 ml) and dichloromethane (250 ml) were added and the mixture was stirred for 30 minutes. The organic phase was washed with water and saturated sodium chloride solution, and dried over magnesium sulfate. After removal of the solvent, the solid residue was recrystallized from 95% ethanol to provide the title product, 6.75 g (60% yield). NMR and IR spectra confirmed the structure.

EXAMPLE XV

6-O-Menthyloxycarbonyl-D-glucose

Benzyl 6-O-menthyloxycarbonyl-β-D-glucoside (2 g, 4.4 mmole) was dissolved in 75 ml of 95% ethanol. A 250 mg quantity of 10% Pd/C was added, and the mixture was hydrogenated under 45 psig for 2 hours. Another 200 mg quantity of catalyst was added and hydrogenation was continued for 20 hours. The catalyst then was removed by filtration and the solvent of the product medium was removed by rotary evaporation under vacuum. The residue was recrystallized from 95% ethanol to provide the title product, 1.5 g (94% yield). NMR and IR spectra confirmed the structure.

EXAMPLE XVI

2,3,4,6-Tetra-O-benzyl-1-O-menthyloxycarbonyl-D-glucose 2,3,4,6-Tetra-O-benzyl-D-glucose, (25 g, 46.3 mmole) and pyridine (10 ml) were dissolved in dichloromethane and the solution was cooled in a ice-acetone bath. Menthyl chloroformate (11.14 g, 50.9 mmole) in 50 ml of dichloromethane was added dropwise over a 30 minute period. The reaction mixture then was stirred at room temperature for about 18 hours. The reaction mixture was poured into 200 ml of ice water and 25 ml of 10% hydrochloric acid. The organic phase was washed with water and saturated sodium chloride solution, and dried over magnesium sulphate. The solvent was removed by rotary evaporation under vacuum, and the residue was purified by column chromatography on silica gel using 5–10% ethyl acetate in hexane as eluent. The product was isolated as an oil, 29 g (87% yield).

NMR and IR spectra confirmed the structure. NMR showed the title product to be a mixture of α- and β-anomers in a 30:70 ratio. The $^{13}$C-chemical shifts for the C-1 carbons were 97.68 ppm for the β-anomer and 93.68 ppm for the α-anomer.

EXAMPLE XVII

1-O-Menthyloxycarbonyl-D-glucopyranose 2,3,4,6-Tetra-O-benzyl-1-O-menthyloxycarbonyl-D-glucose was dissolved in 100 ml of 95% ethanol. Acetic acid (10 ml) and 500 mg of 10% Pd/C were added, and the mixture was hydrogenated under 45 psig for 24 hours. The catalyst was then removed by filtration, and another portion of acetic acid (5 ml) and 10% Pd/C (500 mg) were added. The mixture was hydrogenated at 45 psig of hydrogen for 48 hours. The catalyst then was removed by filtration, and the solvent of the product medium was removed by rotary evaporation under vacuum. The product was isolated by column chromatography as a α/β mixture. NMR and IR spectra confirmed the structure.

Steric Structures of Examples
Menthyloxycarbonylglucoses

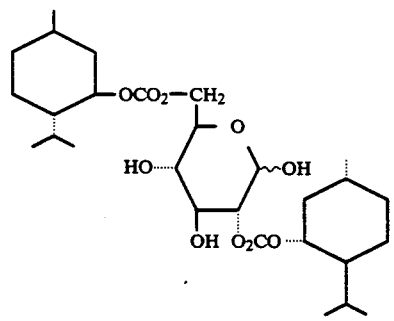

2,6-di-O-menthyloxycarbonyl-D-glucose

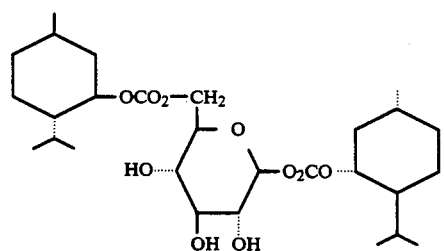

1,6-di-O-menthyloxycarbonyl-β-D-glucopyranose

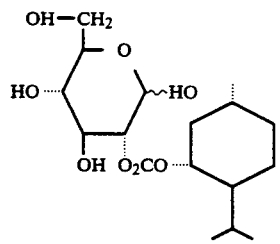

2-O-menthyloxycarbonyl-D-glucose

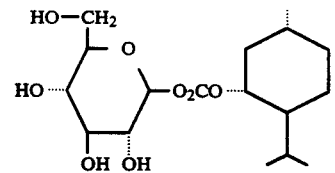

1-O-menthyloxycarbonyl-β-D-glucose

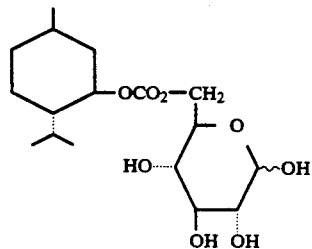

6-O-menthyloxycarbonyl-D-glucose

-continued
Steric Structures of Examples
Menthyloxycarbonylglucoses

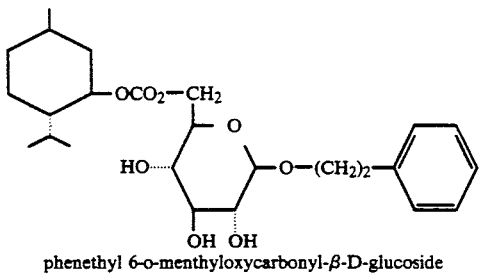
phenethyl 6-o-menthyloxycarbonyl-β-D-glucoside

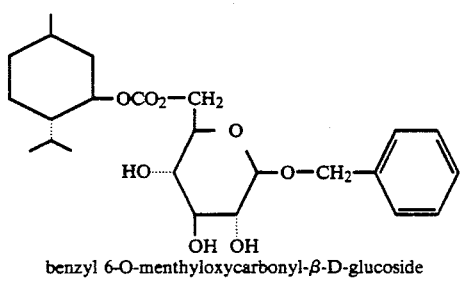
benzyl 6-O-menthyloxycarbonyl-β-D-glucoside

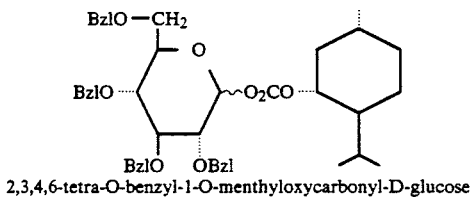
2,3,4,6-tetra-O-benzyl-1-O-menthyloxycarbonyl-D-glucose

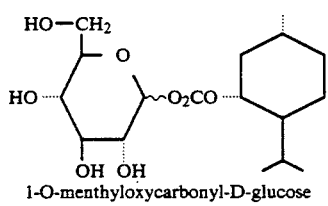
1-O-menthyloxycarbonyl-D-glucose

What is claimed is:

1. A smoking composition comprising an admixture of (1) combustible filler selected from natural tobacco, reconstituted tobacco and tobacco substitutes, and (2) between about 0.0001-5 weight percent, based on the total weight of filler of a menthol-release additive which is a mixture of menthyloxycarbonylglucose compounds comprising (a) more than about 35 mole percent of 1-O-menthyloxycarbonyl-β-D-glucopyranose; (b) more than about 20 mole percent of 1,6-di-O-menthyloxycarbonyl-β-D-glucopyranose; (c) less than about 20 mole percent of 6-O-menthyloxycarbonyl-D-glucose; (d) less than about 15 mole percent of 2-O-menthyloxycarbonyl-D-glucose; and (e) less than about 10 mole percent of 2,6-di-O-menthyloxycarbonyl-D-glucose.

2. A smoking composition in accordance with claim 1 wherein the additive mixture comprises between about 35-65 mole percent of 1-O-menthyloxycarbonyl-β-D-glucopyranose and between about 20-65 mole percent of 1,6-di-O-menthyloxycarbonyl-β-D-glucopyranose.

3. A smoking composition comprising an admixture of (1) combustible filler selected from natural tobacco, reconstituted tobacco and tobacco substitutes, and (2) between about 0.0001-5 weight percent, based on the total weight of filler, of a flavorant-release additive corresponding to the formula:

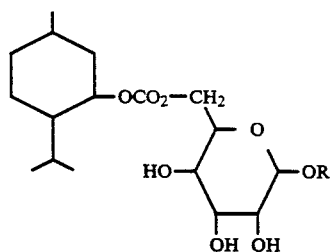

where R is a $C_1$–$C_{10}$ hydrocarbyl substituent.

4. A smoking composition in accordance with claim 3 wherein the additive is phenethyl 6-O-menthyloxycarbonyl-β-D-glucoside.

5. A smoking composition in accordance with claim 3 wherein the additive is benzyl 6-O-menthyloxycarbonyl-β-D-glucoside.

6. A smoking composition comprising an admixture of (1) combustible filler selected from natural tobacco, reconstituted tobacco and tobacco substitutes, and (2) between about 0.0001-5 weight percent, based on the total weight of filler, of a flavorant-release additive comprising 6-O-menthyloxycarbonyl-D-glucose.

7. A smoking composition comprising an admixture of (1) combustible filler selected from natural tobacco, reconstituted tobacco and tobacco substitutes, and (2) between about 0.0001-5 weight percent, based on the total weight weight of filler, of a flavorant-release additive comprising 1-O-menthyloxycarbonyl-D-glucose.

8. A mixture of menthyloxycarbonylglucose compounds comprising (a) more than about 35 mole percent of 1-O-menthyloxycarbonyl-β-D-glucopyranose; (b) more than about 20 mole percent of 1,6-di-O-menthyloxycarbonyl-β-D-glucopyranose; (c) less than about 20 mole percent of 6-O-menthyloxycarbonyl-D-glucose; (d) less than about 15 mole percent of 2-O-menthyloxycarbonyl-D-glucose; and (e) less than about 10 mole percent of 2,6-di-O-menthyloxycarbonyl-D-glucose.

9. A mixture, of menthyloxycarbonylglucose compounds in accordance with claim 8 which contains between about 35-65 mole percent of 1-O-menthyloxycarbonyl-β-D-glucopyranose and between about 20-65 mole percent of 1,6-di-O-menthyloxycarbonyl-β-D-glucopyranose.

10. A mixture of menthyloxycarbonylglucose compounds in accordance with claim 8 which is in the form of a free flowing powder.

11. Phenethyl 6-O-menthyloxycarbonyl-β-D-glucoside.

12. Benzyl 6-O-menthyloxycarbonyl-β-D-glucoside.

13. 2,3,4,6-Tetra-O-benzyl-1-O-menthyloxycarbonyl-D-glucose.

14. A process for producing a mixture of menthyloxycarbonylglucose compounds containing at least about 35 mole percent of 1-O-menthyloxycarbonyl-β-D-glucopyranose which comprises reacting glucose with menthyl chloroformate in an organic solvent medium in contact with a catalyst having the formula:

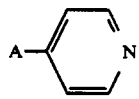

where A is a tertiary amine substituent containing between about 2-6 carbon atoms.

15. A process in accordance with claim 14 wherein the glucose and menthyl chloroformate reactants are present in about equimolar quantities.

16. A process in accordance with claim 14 wherein the menthyl chloroformate and catalyst are present in about equimolar quantities.

17. A process in accordance with claim 14 wherein the catalyst is dimethylaminopyridine.

18. A process in accordance with claim 14 wherein the organic solvent medium comprises pyridine.

19. A process in accordance with claim 14 wherein the organic solvent medium comprises dimethylformamide.

* * * * *